United States Patent [19]

Urich

[11] Patent Number: 5,496,342

[45] Date of Patent: Mar. 5, 1996

[54] ULTRASONIC DEVICE WITH TEMPERATURE SENSING SLEEVE

[76] Inventor: Alex Urich, 27402 Via Caudaloso, Mission Viejo, Calif. 92692

[21] Appl. No.: 326,021

[22] Filed: Oct. 19, 1994

[51] Int. Cl.$^6$ .............................. A61N 7/00; A61B 17/32; G01K 11/00
[52] U.S. Cl. ................................. 606/169; 374/162
[58] Field of Search ...................... 374/162, 209; 604/19, 22; 606/1, 15, 16, 27, 31, 128, 167, 169, 170, 180; 601/2, 3; 128/736

[56] References Cited

U.S. PATENT DOCUMENTS

| | | | |
|---|---|---|---|
| 4,278,349 | 7/1981 | Sander | 374/162 |
| 4,457,633 | 7/1984 | Andrews | 374/209 |
| 4,808,154 | 2/1989 | Freeman | 604/22 |

*Primary Examiner*—Stephen C. Pellegrino
*Assistant Examiner*—Glenn Dawson
*Attorney, Agent, or Firm*—Blakely, Sokoloff, Taylor & Zafman

[57] ABSTRACT

A sleeve that is mounted to the tip of a surgical instrument. The sleeve contains a secondary material that changes color as a function of temperature. The instrument may be an ultrasonic tip that emulsifies tissue. The emulsification of tissue generates heat that raises the temperature of the sleeve. The secondary material changes color when the sleeve temperature exceeds a threshold level, thereby providing an indication of an excessive tissue temperature.

4 Claims, 1 Drawing Sheet

ULTRASONIC DEVICE WITH TEMPERATURE SENSING SLEEVE

BACKGROUND OF THE INVENTION

1. Field of the Invention

The present invention relates to a temperature sensor for the tip of a surgical instrument.

2. Description of Related Art

Surgical procedures are sometimes performed with an ultrasonic instrument that emulsifies tissue. For example, cataracteous lenses are typically emulsified by an ultrasonic tip that is inserted to the cornea of a patient. The vibrating tip of the ultrasonic instrument can generate heat that raises the temperature of the eye.

Conventional ultrasonic interocular instruments have a fluid system which removes the debris created by the vibrating tip and provides a coolant for the eye. It has been found that the debris created by the tip may occlude the aspiration/irrigation system of the instrument. The occlusion may interrupt the cooling process of the procedure and cause the cornea temperature to increase to a level which may damage the eye. It would therefore be desirable to have temperature sensor that provides an indication of when the instrument tip has exceeded a threshold level.

The length of an ultrasonic tip and the thermal inertia of the instrument require that a temperature sensor be located on the tip. Conventional wire thermocouples have a relatively slow response time such that the corneal tissue may become damaged before the surgeon is provided with an indication that the threshold temperature has been exceeded. Additionally, thermocouples are relatively bulky and may affect the operation of the instrument. Although infrared (IR) temperature sensors are not intrusive, IR sensors are relatively inaccurate because of the thermal dispersion in aqueous mediums. It would therefore be desirable to provide a non-intrusive, accurate, responsive, temperature sensor for a surgical instrument.

SUMMARY OF THE INVENTION

The present invention is a sleeve that is mounted to the tip of a surgical instrument. The sleeve contains a secondary material that changes color as a function of temperature. The instrument may be an ultrasonic tip that emulsifies tissue. The emulsification of tissue generates heat that raises the temperature of the sleeve. The secondary material changes color when the sleeve temperature exceeds a threshold level, thereby providing an indication of an excessive tissue temperature.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
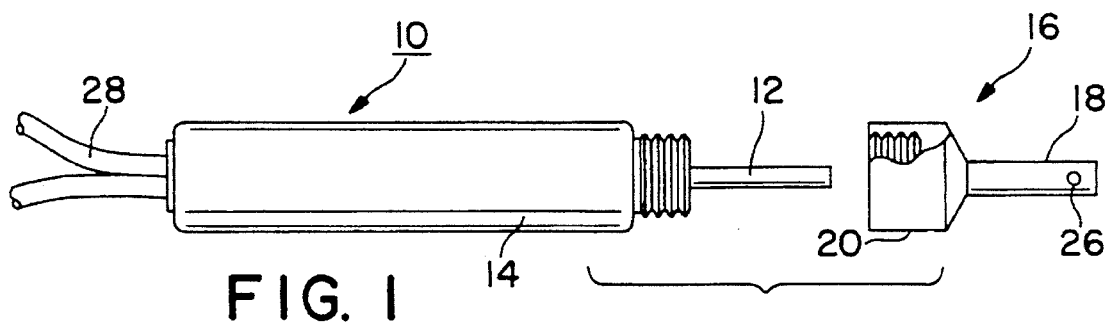
FIG. 1 is an exploded view of a surgical instrument of the present invention.

Referring to the drawings more particularly by reference numbers, FIG. 1 shows a surgical instrument 10 of the present invention. The surgical instrument 10 has a tip 12 that is coupled to an ultrasonic horn 14. The horn 14 moves the tip 12 in a vibratory manner. The vibrating tip 12 can be used to emulsify tissue such as the lens of a cornea. Although tissue emulsification is shown and described, it is to be understood that the instrument 10 can be used for other procedures such as the coagulation of blood. The instrument 10 is typically coupled to an electrical power supply (not shown) that provides an excitation signal to the ultrasonic horn 14. The instrument may have an "on/off" switch (not shown) that allows the surgeon to readily energize and deenergize the vibrating tip 12.

Figure 2:
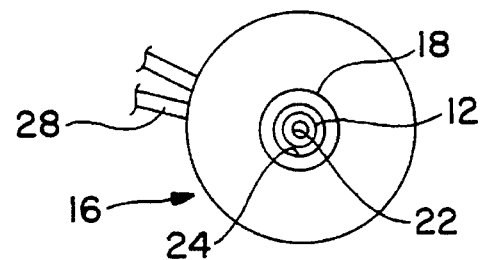
FIG. 2 is an end view of the surgical instrument.

The instrument 10 has a sleeve 16 that is mounted to the tip 12. The sleeve 16 has a shank portion 18 that extends from a base portion 20. The base portion 20 may have an internal thread that screws onto a corresponding thread of the horn 14. As shown in FIG. 2, the tip 12 preferably has an inner aspiration channel 22. The sleeve 16 has an inner diameter that is larger than the outer diameter of the tip 12, so that the tip and sleeve 16 define an irrigation channel 24. The sleeve 16 may have an aperture(s) 26 that is in fluid communication with the irrigation channel 24 and allows irrigation fluid to flow onto the tissue. The instrument 10 is typically coupled to an aspiration/irrigation system 28 that causes a fluid to flow through the irrigation channel 24 and back into the aspiration channel 22 of the tip 12.

The sleeve 16 is constructed from materials that change color as a function of the sleeve temperature. The change in color can provide an indication of the surrounding temperature of the tissue. In the preferred embodiment, the sleeve 16 is constructed from a base material that contains a secondary material that changes color as a function of temperature. By way of example, the secondary material may be liquid crystals or a chromazone powder that is mixed with the base material and then injection molded into a desired shape. In the preferred embodiment, the sleeve is constructed from a composition of 5% chromazone powder and 95% silicone paste, by weight. The chromazone powder and the liquid crystals both become transparent when the temperature of the material exceeds a threshold value. Liquid crystals typically change back to the original color when the temperature raises to yet another threshold value. The liquid crystals may provide an ideal material for applications where the sensor is to sense an absolute temperature or a range of temperatures. For example, coagulation of blood is typically optimized within a certain temperature range. By becoming transparent, a liquid crystal filled sleeve can provide an indication of when the tissue is within the desired temperature range. Likewise, a chromazone powder filled sleeve 16 can provide a permanent indication of when surrounding tissue exceeds a threshold temperature.

The base material is preferably constructed from a non-toxic material such as a silicone. The base material should be of a different color than the secondary material. By way of example, the base material may be white and the secondary material may be black. When the sleeve 16 is below the threshold temperature the sleeve 16 appears black. When the sleeve 16 is above the threshold temperature the secondary material will become transparent and the sleeve 16 will appear white. As another example, the base material may be transparent, the secondary material may be white and the tip may be a highly reflective material that becomes visible when the sleeve exceeds the threshold temperature. The sleeve 16 may be filled with a plurality of different secondary materials that each have a different color and a different threshold temperature. For example, the sleeve may have a first secondary material that is blue and has a threshold temperature of 42° C., and a second secondary material that is red and a threshold temperature of 45° C. Assuming a white base material, the blue portion of the sleeve will turn white when the sleeve temperature exceeds 42° C. and the red portion of the sleeve will turn white when the sleeve temperature exceeds 45° C.

Figure 3:
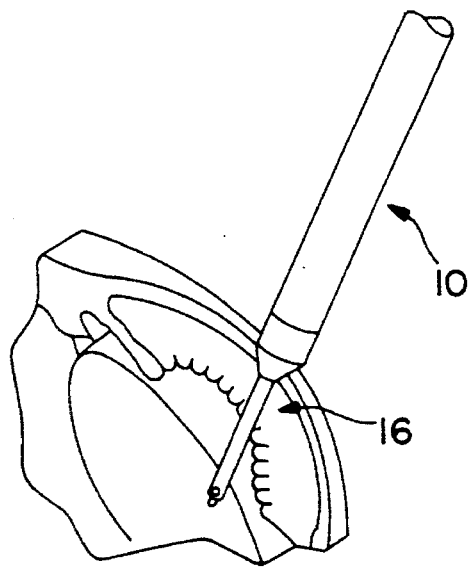
FIG. 3 is a perspective view of the surgical instrument inserted into a cornea.
Figure 4:
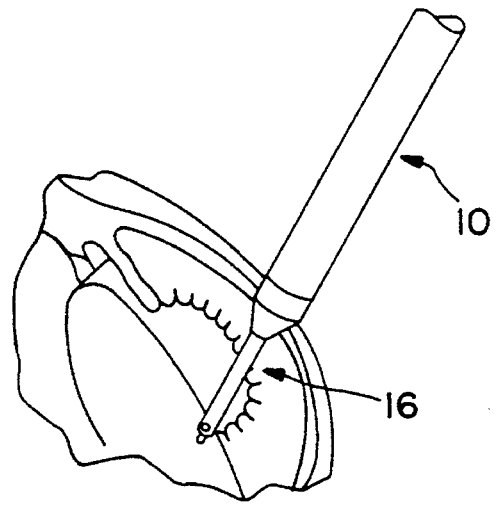
FIG. 4 is a perspective view similar to FIG. 3, showing a sleeve that changed color in response to an increase in temperature.

FIGS. 3 and 4 show the instrument inserted into a cornea to emulsify a lens. The vibratory movement of the tip 12 emulsifies the lens tissue and the aspiration fluid removes the debris through the tip channel 22. If the temperature of the sleeve exceeds a threshold temperature, the secondary material will become transparent and change the color of the sleeve. The change in sleeve color provides the surgeon with an indication that the tissue may be at an undesirable temperature. The surgeon can then de-activate the vibrating tip until the tissue temperature decreases to an acceptable level. An acceptable tissue temperature is indicated by the sleeve changing back to the original color. Although an ultrasonic instrument is shown and described, it is to be understood that the temperature sensor of the present invention can be used with other instruments. Likewise, it is to be understood that the temperature sensor may have shapes other than a sleeve.

Figure 5:
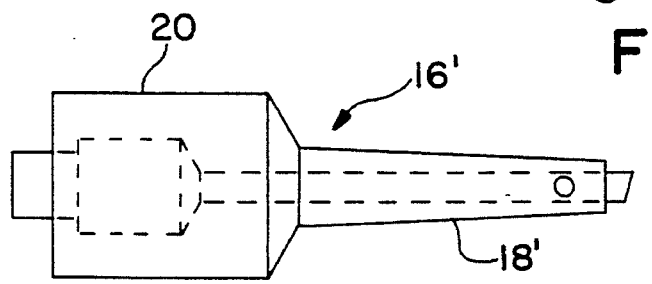
FIG. 5 is a side view of an alternate sleeve embodiment.

FIG. 5 shows an alternate embodiment of a sleeve 16' with a shank portion 18' that tapers toward the base portion 20. The tapered shank portion 18' reduces the entrance effects of the fluid flowing through the irrigation channel. Reducing the entrance effects increases the fluid velocity and the heat transfer rate from the tip.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An ultrasonic instrument, comprising:

a tip;

an ultrasonic horn attached to said tip for moving said tip in a vibratory manner; and, a sleeve that is coupled to the tip, said sleeve including temperature sensing means for changing the color of said sleeve as a function of temperature.

2. The instrument as recited in claim 1, wherein said tip has an inner aspiration channel, and said tip and said sleeve define an irrigation channel therebetween.

3. The instrument as recited in claim 2, wherein said sleeve has an irrigation aperture.

4. The instrument as recited in claim 1, wherein said temperature sensing means includes the sleeve having a base material which contains a second material that changes color as a function of temperature.

* * * * *